United States Patent
Zhou et al.

(10) Patent No.: US 10,494,383 B2
(45) Date of Patent: Dec. 3, 2019

(54) METHOD FOR PREPARING DIFLUOROALLYLBORONATE AND APPLICATION THEREOF

(71) Applicant: DALIAN UNIVERSITY OF TECHNOLOGY, Dalian, Liaoning (CN)

(72) Inventors: Yuhan Zhou, Liaoning (CN); Jingping Qu, Liaoning (CN); Yang Liu, Liaoning (CN); Yilong Zhao, Liaoning (CN)

(73) Assignee: DALIAN UNIVERSITY OF TECHNOLOGY, Dalian, Liaoning (CN)

(*) Notice: Subject to any disclaimer, the term of this patent is extended or adjusted under 35 U.S.C. 154(b) by 0 days.

(21) Appl. No.: 16/300,257

(22) PCT Filed: Jun. 23, 2017

(86) PCT No.: PCT/CN2017/089694
§ 371 (c)(1),
(2) Date: Nov. 9, 2018

(87) PCT Pub. No.: WO2018/024046
PCT Pub. Date: Feb. 8, 2018

(65) Prior Publication Data
US 2019/0144469 A1    May 16, 2019

(30) Foreign Application Priority Data
Aug. 4, 2016    (CN) .......................... 2016 1 0635012

(51) Int. Cl.
| | |
|---|---|
| *C07C 45/40* | (2006.01) |
| *C07C 45/68* | (2006.01) |
| *C07C 69/74* | (2006.01) |
| *C07F 5/00* | (2006.01) |
| *C07F 5/02* | (2006.01) |
| *C07C 69/76* | (2006.01) |

(52) U.S. Cl.
CPC ............... *C07F 5/02* (2013.01); *C07C 45/40* (2013.01); *C07C 45/68* (2013.01); *C07C 69/76* (2013.01); *C07F 5/025* (2013.01); *C07C 2603/74* (2017.05)

(58) Field of Classification Search
CPC ......... C07C 45/40; C07C 45/68; C07C 69/76; C07F 5/02; C07F 5/025
See application file for complete search history.

(56) References Cited

U.S. PATENT DOCUMENTS 3,080,405 A    3/1963 Larsen et al.

FOREIGN PATENT DOCUMENTS

| CN | 104892655 A | 9/2015 |
| CN | 105017299 A | 11/2015 |
| EP | 2647640 A1 | 10/2013 |
| WO | 2012129384 A2 | 9/2012 |

OTHER PUBLICATIONS

Sei-Ichi Hayashi et al., "Convenient Procedures for Conversion of Carbonyl Compounds to gem-Difluoroolefins and Their Selective Reductions to Monofluoroolefins", Chemistry Letters, 1979, pp. 983-986.

(Continued)

*Primary Examiner* — Sikarl A Witherspoon
(74) *Attorney, Agent, or Firm* — Novick, Kim & Lee, PLLC; Allen Xue

(57) ABSTRACT

The present invention relates to a method for preparing difluoroallylboronate and application thereof, and it belongs to a field of compound preparation. A method for preparing difluoroallyl borate ester is using a compound of the formula II and bis (pinacolato) diboron as raw materials in a solvent and in the presence of an iron catalyst and a base according to the following reaction formula, to obtain a compound of the formula I,

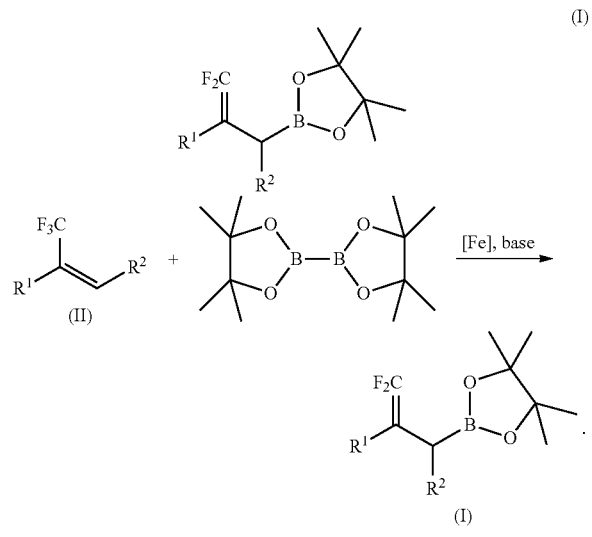

The method of the present invention directly use an inexpensive, commercially available metal iron salt as a catalyst to provide a convenient, low-cost method for preparing difluoroallyl borate ester, and provide a new and effective approach for the synthesis of γ-aminobutyric acid receptor agonist (III).

10 Claims, No Drawings

(56) References Cited

OTHER PUBLICATIONS

William B. Motherwell et al., "A Convenient Method for Replacement of the Anomeric Hydroxy Group in Carbohydrates by Difluoromethyl Functionality", J. Chem. Soc., Chem. Commun., 1989, pp. 1437-1439.

Ba V. Nguyen et al., "A New Route for the Preparation of Substituted 2,2-Difluorostyrenes and a Convenient Rounte to Substituted (2,2,2-Trifluoroethyl)Benzenes", J. Org. Chem., 1997, vol. 62, pp. 7758-7764.

Kohei Fuchibe et al., "Substitution of Two Fluorine Atoms in a Trifluoromethly Group: Regioselective Synthesis of 3-Fluoropyrazoles", Angewandte Chemie International Edition, 2012, vol. 51, pp. 12059-12062.

Iwao Qjima, "Fluorine in Medicinal Chemistry and Chemical Biology", Wiley-Blackwell: West Sussex, UK, 2009.

Dennis G. Hall, "Boronic Acids: Preparation and Applications in Organic Synthesis and Medicine", Wiley-VCH, Weinheim, 2005.

Mark D. Greenhalgh et al., "Chemo-, regio-, and stereoselective iron-catalysed hydroboration of alkenes and alkynes", Chem. Commun., 2013, vol. 49, pp. 11230-11232.

Akira Suzuki, "Cross-Coupling Reactions of Organoboranes: An Easy Way to Construct C—C bonds (Nobel Lecture)", Angew, Chem. Int. Ed. 2011, (vol. 50), pp. 6723-6737.

Rosa Corberan et al., "NHC-Cu-Catalyzed Enantioselective Hydroboration of Acyclic and Exocyclic 1, 1-Disubstituted Aryl Alkenes", Angew, Chem. Int. Ed. 2011, (vol. 50), pp. 7079-7082.

Changho Han et al., "Evaluation of Difluoromethyl Ketones as Agonists of the γ-Aminobutyric Acid Type B (GABAB) Receptor", Journal of Medicinal Chemistry, 2013, vol. 56, pp. 2456-2465.

Changho Han et al., "Cleavage of Carbon-Carbon Bonds through the Mild Release of Trifluoroacetate: Generation of α,α-Difluoroenolates for Aldol Reactions", Journal of the American Chemical Society, 2011, vol. 133, pp. 5802-5805.

METHOD FOR PREPARING DIFLUOROALLYLBORONATE AND APPLICATION THEREOF

TECHNICAL FIELD

The present invention relates to a method for preparing difluoroallylboronate and application thereof. It belongs to the field of compound preparation.

BACKGROUND ART

Generally, the introduction of fluorine atom(s) into an organic molecule can change the physical, chemical properties and biological activity of a compound. Therefore, introduction of fluorine atom(s) into various drugs, macromolecular materials and liquid crystal materials is a commonly used technique for improving the properties of a substance.

1,1-difluorovinyl are an important class of fluorine-containing groups, which are often used in the construction of fluorine-containing skeleton. functional group of 1,1-difluorovinyl can be defluorinated to form monofluoroolefins (*Chem. Lett.* 1979, 983.), hydrogenated to form difluoromethyl (*J. Chem. Soc., Chem. Commun.* 1989, 1437.), fluorinated to form trifluoromethyl (*J. Org. Chem.* 1997, 62, 7758.). The unsaturated double bond can also undergo a nucleophilic addition reaction to form a fluorine-containing heterocyclic ring by intermolecular cycloaddition (*Angew. Chem. Int Ed.* 2012, 51, 12059.). In addition, functional group of the 1,1-difluorovinyl is considered to be a carbonyl bioisostere in aspect of drug design (*J. Chem. Soc., Chem. Commun.* 1989, 1437.). The organic molecules containing 1,1-difluorovinyl functional group are often used as enzyme inhibitors (*Fluorine in Medicinal Chemistry and Chemical Biology*; Wiley-Blackwell: West Sussex, UK, 2009.). Therefore, it is particularly important to simply synthesize organic molecules containing functional group of 1,1-difluorovinyl.

Alkyl borate and alkylboric acid are very important intermediates in the field of organic synthesis (*Boronic Acids: Preparation and Applications in Organic Synthesis and Medicine*, Wiley-VCH, Weinheim, 2005), which are widely used in the synthesis of various drugs, macromolecular materials, liquid crystal materials and fluorescent probe materials. Compounds containing functional groups of borate or boric acid can be easily converted to corresponding alcohols, aldehydes, amine functional groups (*Chem. Commun.* 2013, 49, 11230.), in addition to the classical Suzuki-Miyaura coupling (*Angew. Chem., Int. Ed.* 2011, 50, 6722.). Most compounds containing functional groups of borate or boric acid have good stability compared to other metal organic nucleophilic reagent (such as Grignard reagent), and can be purified or stored directly under air atmosphere, thus it is of great significance to synthesize borate or boric acid compounds with diversiform functional groups.

The difluoroallylboronate compound containing both 1,1-difluorovinyl functional groups and borate functional groups in the molecule is an excellent organic synthetic block, but there is only one case reported about the synthesis of difluoroallylboronate compounds (*Angew. Chem. Int. Ed.* 2011, 50, 7079), and this method requires a complex carbene copper complex as a catalyst and the yield is low.

3-(4-acetylphenyl)-1-((3r,5r,7r)-adamantine-1-yl)-2,2-difluoro-3-hydroxypropan-1-one (Compound III) is a γ-aminobutyric acid receptor agonist (*J. Med. Chem.* 2013, 56, 2456). In the existing synthetic route, 1-((3r,5r,7r)-adamantan-1-yl)-4,4,4-trifluoro-3-hydroxy-1-butanone is used as raw material, after fluorination with Selectfluor, detrifluoroacetyl group and addition with aldehydes, it is obtained. The reagent used is relatively expensive (*J. Am. Chem. Soc.* 2011, 133, 5802).

SUMMARY OF THE INVENTION

The present disclosure aims to provide an efficient, simple and economical method for synthesizing difluoroallylboronate compounds (compounds of formula II) using an inexpensive, commercially available iron salt as a catalyst, bis (pinacolato) diboron as a borylation reagent and trifluoromethylene (a compound of formula I) as a raw material, and their applications in the synthesis of γ-aminobutyric acid receptor agonists.

A method for preparing difluoroallylboronate is to react a compound of the formula II and bis (pinacolato) diboron in a solvent in the presence of an iron catalyst and a base according to the following reaction formula, to obtain a compound of the formula I,

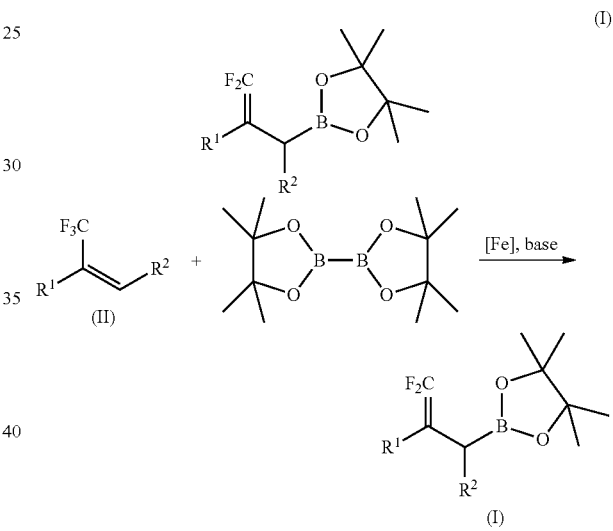

wherein,
R$^1$ is selected from (C1-C10) alkyl,

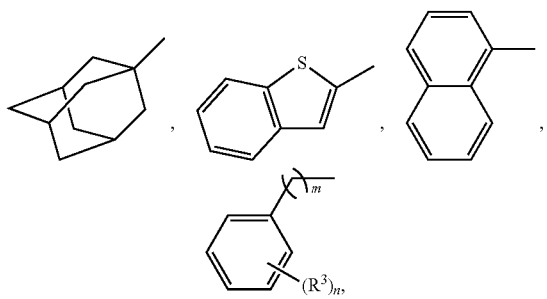

wherein, m=0-4, n=1-5;
R$^2$ is selected from H, (C1-C6) alkyl;
R$^3$ is selected from H, (C1-C6) alkyl, phenyl, halogen, trifluoromethyl, trifluoromethoxy, (C1-C4) alkoxyl, (C2-C5) ester group.

the iron catalyst is at least one of ferrous chloride, ferric chloride, ferrous bromide, ferric bromide, ferric acetylacetonate, ferrous acetylacetonate, and ferrous acetate.

the base is selected from at least one of potassium t-butoxide, sodium t-butoxide, lithium t-butoxide, sodium methoxide, lithium methoxide, potassium methoxide, cesium carbonate, potassium carbonate, sodium carbonate, sodium hydroxide, potassium hydroxide, potassium phosphate.

The solvent of the present invention is preferably at least one of tetrahydrofuran (THF), acetonitrile, N,N-dimethylformamide, toluene, dichloromethane, 1,2-dichloromethane, anisole, methyl tert-butyl ether (MTBE), dioxane and glycol dimethyl ether.

The solvent of the present invention may be used in an amount satisfying the reaction requirements. Preferably, the ratio of the amount of compound of the formula II to the solvent is 1 mmol 5-15 mL.

Unless otherwise stated, the terms used herein have the following meanings.

The term "alkyl" as used herein includes both linear alkyl and branched alkyl. When referring to a single alkyl such as "propyl", it specifically refers to linear alkyl, and when referring to a single branched alkyl such as "isopropyl", it specifically refers to branched alkyl. For example, "alkyl below C4" includes methyl, ethyl, n-propyl, isopropyl, n-butyl, t-butyl, etc. Similar rules apply to other groups used in this specification.

The term "halogen" used herein includes fluorine, chlorine, bromine, iodine.

The (C2-C5) ester group herein is a group having the following structure: —COOR, wherein R is (C1-C4) alkyl.

The (C1-C4) alkoxy herein is a group having the following structure: —O-$M_1$, wherein $M_1$ is (C1-C4) alkyl such as methoxyl, oxethyl, propoxyl, isopropoxyl, butoxyl, tert-butoxyl.

In the foregoing technical solution, for the

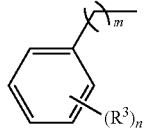

(m=0-4, n=1-5), wherein, in $(R^3)_n$, n=1-5 means that the substitution of $R^3$ on the phenyl group may be a mono- or poly-substitution, and may be 1, 2, 3, 4 or 5 substitutions. When n=1, it is monosubstituted, the monosubstituted positions may be position 2, 3 or 4; when n=2, 3, 4 or 5, it is polysubstituted, wherein, when n=2, it is disubstituted, disubstituted positions are 2,3-, 2,4-, 2,5-, 2,6-, 3,4-, 3,5-; when n=3, it is tri-substitution, and the positions of the tri-substitution are 2,3.4-, 2,3,5-, 2,3,6-, 3,4,5-.

In the difluoroallylboronate preparation method herein, preferably $R^1$ is selected from (C1-C10) alkyl,

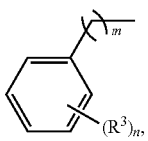

wherein m=0, 1, 2, 3, 4, preferably m=0 or 2, n=1, 2, 3, 4, 5;

$R^2$ is selected from H, (C1-C6) alkyl, further $R^2$ is preferably H, n-propyl;

$R^3$ is selected from H, (C1-C6) alkyl, phenyl, halogen, trifluoromethyl, trifluoromethoxyl, (C1-C4) alkoxyl, (C2-05) ester group; further, $R^3$ is preferably H, methyl, methoxy, halogen, trifluoromethyl, tert-butyl, trifluoromethoxyl, phenyl;

For the method for preparing difluoroallylboronate in the present disclosure, preferably the amount of substance of the base is 0.5 to 3 times of that of the compound of formula II, further preferably, the amount of substance of the base is 1 to 2 times of that of the compound of formula II.

For the method for preparing difluoroallylboronate in the present invention, preferably the amount of substance of the bis(pinacolato)diboron is 1 to 3 times of that of the compound of formula II, further, preferably the amount of substance of the bis(pinacolato)diboron is 1 to 1.5 times of that of the compound of formula II.

For the method for preparing difluoroallylboronate in the present invention, preferably, the amount of substance of the catalyst is 0.1% to 10% of that of the compound of formula II, preferably 5%-10%.

For the method for preparing difluoroallylboronate in the present invention, preferably the reaction temperature of the reaction is 25° C. to solvent reflux temperature, and the reaction time is 10 min-48 h, preferably 5 h-24 h.

A preferred technical solution in the present invention:

A method for preparing difluoroallylboronate is to react a compound of the formula II and bis (pinacolato) diboron in a solvent in the presence of an iron catalyst and a base according to the following reaction formula, to obtain a compound of the formula I, wherein the reaction temperature of the reaction is 25° C. to solvent reflux temperature, and the reaction time is 10 min-48 h,

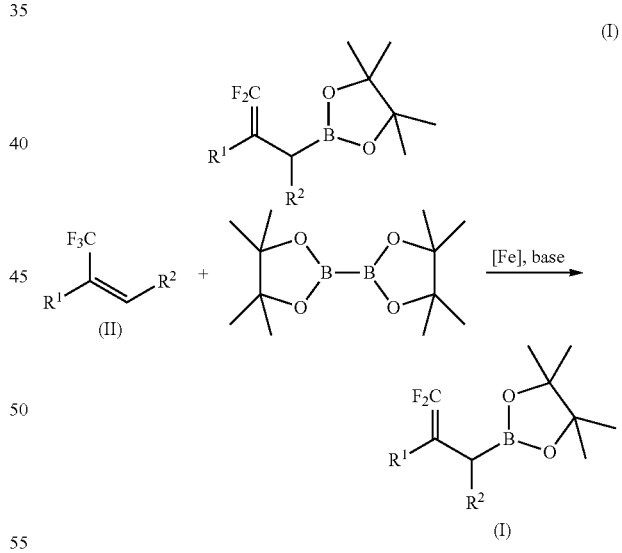

wherein, $R^1$ is selected from (C1-C10) alkyl,

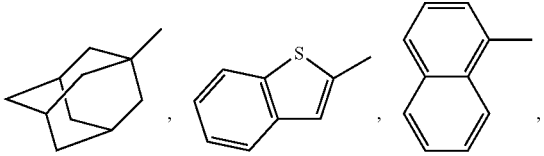

-continued

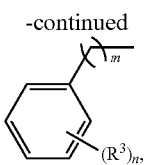

wherein, m=0-4, n=1-5;

$R^2$ is selected from H, (C1-C6) alkyl;

$R^3$ is selected from H, (C1-C6) alkyl, phenyl, halogen, trifluoromethyl, trifluoromethoxy, (C1-C4) alkoxyl, (C2-C5) ester;

the iron catalyst is at least one of ferrous chloride, ferric chloride, ferrous bromide, ferric bromide, ferric acetylacetonate, ferrous acetylacetonate, and ferrous acetate.

the base is selected from at least one of potassium t-butoxide, sodium t-butoxide, lithium t-butoxide, sodium methoxide, lithium methoxide, potassium methoxide, cesium carbonate, potassium carbonate, sodium carbonate, sodium hydroxide, potassium hydroxide, potassium phosphate.

The solvent is selected from at least one of tetrahydrofuran (THF), acetonitrile, N,N-dimethylformamide, toluene, dichloromethane, 1,2-dichloromethane, anisole, methyl tert-butyl ether (MTBE), dioxane, glycol dimethyl ether.

Another object of the present invention is to provide applications of the compound prepared by the foregoing synthesis method in synthesizing γ-aminobutyric acid receptor agonist (III).

A preparation method for synthesizing γ-aminobutyric acid receptor agonist (III) using difluoroallylboronate as a raw material, firstly synthesizing 2-(2-((3r,5r,7r)-adamantan-1-yl)-3,3-difluoroallyl)-4,4,5,5-tetramethyl-1,3,2-dioxaborolane according to the foregoing method, and then performing the following route:

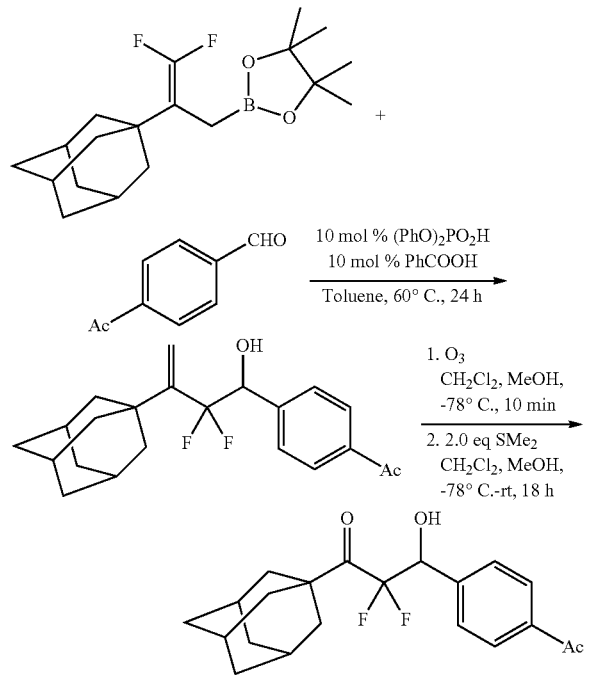

Including the following two-step reaction:

① in toluene solvent, 2-(2-((3r,5r,7r)-adamantan-1-yl)-3,3-difluoroallyl)-4,4,5,5-tetramethyl-1,3,2-dioxaborolane and 4-acetylbenzaldehyde react at 60° C. for 10 h-30 h under the catalysis of diphenyl phosphate and benzoic acid, with a molar ratio of 2-(2-((3r,5r,7r)-adamantan-1-yl)-3,3-difluoroallyl)-4,4,5,5-tetramethyl-1,3,2-dioxaborolane, 4-acetylbenzaldehyde, diphenyl phosphate and benzoic acid at 1:(1-1.5):0.1:0.1;

② dissolve 1-(4-(3-((3r,5r,7r)-adamantan-1-yl)-2,2-difluoro-1-hydroxybut-3-en-1-yl)phenyl)ethanone in dichloromethane/methanol mixed solvent, introduce ozone by bubbling at −78° C. and maintain the colour of blue for 10 min, then move them at room temperature and introduce argon by bubbling until the reaction system become a colorless clear solution; then cool them to −78° C. again and add dimethyl sulfide under the argon atmosphere, naturally rise to room temperature and react for 10 h-24 h; the molar ratio of 1-(4-(3-((3r,5r,7r)-adamantan-1-yl)-2,2-difluoro-1-hydroxybut-3-en-1-yl)phenyl)ethanone and dimethyl sulfide is 1:2, and the volume ratio of dichloromethane and methanol in the mixed solvent is 1:1-3:1.

Table 1 lists the specific structures of the substituents of the respective starting compounds in the above reaction formula.

TABLE 1

| $R^1$ | $R^2$ |
|---|---|
| benzothiophen-2-ylmethyl | H |
| naphthalen-1-ylmethyl | H |
| Ph— | H |
| 2-MeO—C$_6$H$_4$— | H |
| 3-MeO—C$_6$H$_4$— | H |
| 4-MeO—C$_6$H$_4$— | H |
| 2-EtO—C$_6$H$_4$— | H |
| 3-EtO—C$_6$H$_4$— | H |
| 4-EtO—C$_6$H$_4$— | H |
| 2-$^n$PrO—C$_6$H$_4$— | H |
| 3-$^n$PrO—C$_6$H$_4$— | H |
| 4-$^n$PrO—C$_6$H$_4$— | H |
| 2-$^i$PrO—C$_6$H$_4$— | H |
| 3-$^i$PrO—C$_6$H$_4$— | H |
| 4-$^i$PrO—C$_6$H$_4$— | H |
| 2-$^n$BuO—C$_6$H$_4$— | H |
| 3-$^n$BuO—C$_6$H$_4$— | H |
| 4-$^n$BuO—C$_6$H$_4$— | H |
| 2-$^i$BuO—C$_6$H$_4$— | H |
| 3-$^i$BuO—C$_6$H$_4$— | H |
| 4-$^i$BuO—C$_6$H$_4$— | H |
| 2-$^t$BuO—C$_6$H$_4$— | H |
| 3-$^t$BuO—C$_6$H$_4$— | H |
| 4-$^t$BuO—C$_6$H$_4$— | H |
| 2-F—C$_6$H$_4$— | H |
| 3-F—C$_6$H$_4$— | H |
| 4-F—C$_6$H$_4$— | H |
| 2-Cl—C$_6$H$_4$— | H |
| 3-Cl—C$_6$H$_4$— | H |
| 4-Cl—C$_6$H$_4$— | H |
| 2-Br—C$_6$H$_4$— | H |
| 3-Br—C$_6$H$_4$— | H |
| 4-Br—C$_6$H$_4$— | H |
| 2-F$_3$C—C$_6$H$_4$— | H |

TABLE 1-continued

| R$^1$ | R$^2$ |
|---|---|
| 3-F$_3$C—C$_6$H$_4$— | H |
| 4-F$_3$C—C$_6$H$_4$— | H |
| 2-F$_3$CO—C$_6$H$_4$— | H |
| 3-F$_3$CO—C$_6$H$_4$— | H |
| 4-F$_3$CO—C$_6$H$_4$— | H |
| 2-Me—C$_6$H$_4$— | H |
| 3-Me—C$_6$H$_4$— | H |
| 4-Me—C$_6$H$_4$— | H |
| 2-Et—C$_6$H$_4$— | H |
| 3-Et—C$_6$H$_4$— | H |
| 4-Et—C$_6$H$_4$— | H |
| 2-$^n$Pr—C$_6$H$_4$— | H |
| 3-$^n$Pr—C$_6$H$_4$— | H |
| 4-$^n$Pr—C$_6$H$_4$— | H |
| 2-$^i$Pr—C$_6$H$_4$— | H |
| 3-$^i$Pr—C$_6$H$_4$— | H |
| 4-$^i$Pr—C$_6$H$_4$— | H |
| 2-$^n$Bu—C$_6$H$_4$— | H |
| 3-$^n$Bu—C$_6$H$_4$— | H |
| 4-$^n$Bu—C$_6$H$_4$— | H |
| 2-$^i$Bu—C$_6$H$_4$— | H |
| 3-$^i$Bu—C$_6$H$_4$— | H |
| 4-$^i$Bu—C$_6$H$_4$— | H |
| 2-$^s$Bu—C$_6$H$_4$— | H |
| 3-$^s$Bu—C$_6$H$_4$— | H |
| 4-$^s$Bu—C$_6$H$_4$— | H |
| 4-Ph—C$_6$H$_4$— | H |
| 2-MeOOC—C$_6$H$_4$— | H |
| 3-MeOOC—C$_6$H$_4$— | H |
| 4-MeOOC—C$_6$H$_4$— | H |
| 2-EtOOC—C$_6$H$_4$— | H |
| 3-EtOOC—C$_6$H$_4$— | H |
| 4-EtOOC—C$_6$H$_4$— | H |
| 2-$^n$PrOOC—C$_6$H$_4$— | H |
| 3-$^n$PrOOC—C$_6$H$_4$— | H |
| 4-$^n$PrOOC—C$_6$H$_4$— | H |
| 2-$^i$PrOOC—C$_6$H$_4$— | H |
| 3-$^i$PrOOC—C$_6$H$_4$— | H |
| 4-$^i$PrOOC—C$_6$H$_4$— | H |
| 2-$^n$BuOOC—C$_6$H$_4$— | H |
| 3-$^n$BuOOC—C$_6$H$_4$— | H |
| 4-$^n$BuOOC—C$_6$H$_4$— | H |
| 2-$^i$BuOOC—C$_6$H$_4$— | H |
| 3-$^i$BuOOC—C$_6$H$_4$— | H |
| 4-$^i$BuOOC—C$_6$H$_4$— | H |
| 2-$^s$BuOOC—C$_6$H$_4$— | H |
| 3-$^s$BuOOC—C$_6$H$_4$— | H |
| 4-$^s$BuOOC—C$_6$H$_4$— | H |
| 2-Me-3-Me-C$_6$H$_3$— | H |
| 2-Me-4-Me-C$_6$H$_3$— | H |
| 2-Me-5-Me-C$_6$H$_3$— | H |
| 2-Me-6-Me-C$_6$H$_3$— | H |
| 3-Me-4-Me-C$_6$H$_3$— | H |
| 3-Me-5-Me-C$_6$H$_3$— | H |
| 3-Me-6-Me-C$_6$H$_3$— | H |
| 2-MeO-3-MeO—C$_6$H$_3$— | H |
| 2-MeO-4-MeO—C$_6$H$_3$— | H |
| 2-MeO-5-MeO—C$_6$H$_3$— | H |
| 2-MeO-6-MeO—C$_6$H$_3$— | H |
| 3-MeO-4-MeO—C$_6$H$_3$— | H |
| 3-MeO-5-MeO—C$_6$H$_3$— | H |
| 3-MeO-6-MeO—C$_6$H$_3$— | H |
| Ph—CH$_2$CH$_2$— | H |
| Ph—CH$_2$CH$_2$CH$_2$— | H |
| Ph—CH$_2$CH$_2$CH$_2$CH$_2$— | H |
| CH$_3$(CH$_2$)$_8$— | H |
| CH$_3$(CH$_2$)$_7$— | H |
| CH$_3$(CH$_2$)$_6$— | H |
| CH$_3$(CH$_2$)$_5$— | H |
| CH$_3$(CH$_2$)$_4$— | H |
| CH$_3$(CH$_2$)$_3$— | H |
| CH$_3$(CH$_2$)$_9$— | H |
| (CH$_3$)$_2$CH(CH$_2$)$_7$— | H |
| (CH$_3$)$_2$CH(CH$_2$)$_6$— | H |
| (CH$_3$)$_2$CH(CH$_2$)$_5$— | H |
| (CH$_3$)$_2$CH(CH$_2$)$_4$— | H |
| (CH$_3$)$_2$CH(CH$_2$)$_3$— | H |
| (CH$_3$)$_2$CH(CH$_2$)$_2$— | H |
| (CH$_3$)$_3$C(CH$_2$)$_6$— | H |
| (CH$_3$)$_3$C(CH$_2$)$_5$— | H |
| (CH$_3$)$_3$C(CH$_2$)$_4$— | H |
| (CH$_3$)$_3$C(CH$_2$)$_3$— | H |
| (CH$_3$)$_3$C(CH$_2$)$_2$— | H |
| CH$_3$(CH$_2$)$_7$(CH$_3$)CH— | H |
| CH$_3$(CH$_2$)$_6$(CH$_3$)CH— | H |
| CH$_3$(CH$_2$)$_5$(CH$_3$)CH— | H |
| CH$_3$(CH$_2$)$_4$(CH$_3$)CH— | H |
| CH$_3$(CH$_2$)$_3$(CH$_3$)CH— | H |
| CH$_3$(CH$_2$)$_2$(CH$_3$)CH— | H |
| CH$_3$(CH$_2$)$_6$(CH$_3$)CHCH$_2$— | H |
| CH$_3$(CH$_2$)$_5$(CH$_3$)CHCH$_2$— | H |
| CH$_3$(CH$_2$)$_4$(CH$_3$)CHCH$_2$— | H |
| CH$_3$(CH$_2$)$_3$(CH$_3$)CHCH$_2$— | H |
| CH$_3$(CH$_2$)$_2$(CH$_3$)CHCH$_2$— | H |
| Ph— | $^n$Pr— |
| 2-MeO—C$_6$H$_4$— | $^n$Pr— |
| 3-MeO—C$_6$H$_4$— | $^n$Pr— |
| 4-MeO—C$_6$H$_4$— | $^n$Pr— |
| 2-EtO—C$_6$H$_4$— | $^n$Pr— |
| 3-EtO—C$_6$H$_4$— | $^n$Pr— |
| 4-EtO—C$_6$H$_4$— | $^n$Pr— |
| 2-$^n$PrO—C$_6$H$_4$— | $^n$Pr— |
| 3-$^n$PrO—C$_6$H$_4$— | $^n$Pr— |
| 4-$^n$PrO—C$_6$H$_4$— | $^n$Pr— |
| 2-$^i$PrO—C$_6$H$_4$— | $^n$Pr— |
| 3-$^i$PrO—C$_6$H$_4$— | $^n$Pr— |
| 4-$^i$PrO—C$_6$H$_4$— | $^n$Pr— |
| 2-$^n$BuO—C$_6$H$_4$— | $^n$Pr— |
| 3-$^n$BuO—C$_6$H$_4$— | $^n$Pr— |
| 4-$^n$BuO—C$_6$H$_4$— | $^n$Pr— |
| 2-$^i$BuO—C$_6$H$_4$— | $^n$Pr— |
| 3-$^i$BuO—C$_6$H$_4$— | $^n$Pr— |
| 4-$^i$BuO—C$_6$H$_4$— | $^n$Pr— |
| 2-$^s$BuO—C$_6$H$_4$— | $^n$Pr— |
| 3-$^s$BuO—C$_6$H$_4$— | $^n$Pr— |
| 4-$^s$BuO—C$_6$H$_4$— | $^n$Pr— |
| 2-F—C$_6$H$_4$— | $^n$Pr— |
| 3-F—C$_6$H$_4$— | $^n$Pr— |
| 4-F—C$_6$H$_4$— | $^n$Pr— |
| 2-Cl—C$_6$H$_4$— | $^n$Pr— |
| 3-Cl—C$_6$H$_4$— | $^n$Pr— |
| 4-Cl—C$_6$H$_4$— | $^n$Pr— |
| 2-Br—C$_6$H$_4$— | $^n$Pr— |
| 3-Br—C$_6$H$_4$— | $^n$Pr— |
| 4-Br—C$_6$H$_4$— | $^n$Pr— |
| 2-F$_3$C—C$_6$H$_4$— | $^n$Pr— |
| 3-F$_3$C—C$_6$H$_4$— | $^n$Pr— |
| 4-F$_3$C—C$_6$H$_4$— | $^n$Pr— |
| 2-F$_3$CO—C$_6$H$_4$— | $^n$Pr— |
| 3-F$_3$CO—C$_6$H$_4$— | $^n$Pr— |
| 4-F$_3$CO—C$_6$H$_4$— | $^n$Pr— |
| 2-Me—C$_6$H$_4$— | $^n$Pr— |
| 3-Me—C$_6$H$_4$— | $^n$Pr— |
| 4-Me—C$_6$H$_4$— | $^n$Pr— |
| 2-Et—C$_6$H$_4$— | $^n$Pr— |
| 3-Et—C$_6$H$_4$— | $^n$Pr— |
| 4-Et—C$_6$H$_4$— | $^n$Pr— |
| 2-$^n$Pr—C$_6$H$_4$— | $^n$Pr— |
| 3-$^n$Pr—C$_6$H$_4$— | $^n$Pr— |
| 4-$^n$Pr—C$_6$H$_4$— | $^n$Pr— |
| 2-$^i$Pr—C$_6$H$_4$— | $^n$Pr— |
| 3-$^i$Pr—C$_6$H$_4$— | $^n$Pr— |
| 4-$^i$Pr—C$_6$H$_4$— | $^n$Pr— |
| 2-$^n$Bu—C$_6$H$_4$— | $^n$Pr— |
| 3-$^n$Bu—C$_6$H$_4$— | $^n$Pr— |
| 4-$^n$Bu—C$_6$H$_4$— | $^n$Pr— |
| 2-$^i$Bu—C$_6$H$_4$— | $^n$Pr— |
| 3-$^i$Bu—C$_6$H$_4$— | $^n$Pr— |
| 4-$^i$Bu—C$_6$H$_4$— | $^n$Pr— |
| 2-$^s$Bu—C$_6$H$_4$— | $^n$Pr— |
| 3-$^s$Bu—C$_6$H$_4$— | $^n$Pr— |
| 4-$^s$Bu—C$_6$H$_4$— | $^n$Pr— |
| 4-Ph—C$_6$H$_4$— | $^n$Pr— |
| 2-MeOOC—C$_6$H$_4$— | $^n$Pr— |
| 3-MeOOC—C$_6$H$_4$— | $^n$Pr— |
| 4-MeOOC—C$_6$H$_4$— | $^n$Pr— |

TABLE 1-continued

| R¹ | R² |
|---|---|
| 2-EtOOC—C₆H₄— | ⁿPr— |
| 3-EtOOC—C₆H₄— | ⁿPr— |
| 4-EtOOC—C₆H₄— | ⁿPr— |
| 2-ⁿPrOOC—C₆H₄— | ⁿPr— |
| 3-ⁿPrOOC—C₆H₄— | ⁿPr— |
| 4-ⁿPrOOC—C₆H₄— | ⁿPr— |
| 2-ⁱPrOOC—C₆H₄— | ⁿPr— |
| 3-ⁱPrOOC—C₆H₄— | ⁿPr— |
| 4-ⁱPrOOC—C₆H₄— | ⁿPr— |
| 2-ⁿBuOOC—C₆H₄— | ⁿPr— |
| 3-ⁿBuOOC—C₆H₄— | ⁿPr— |
| 4-ⁿBuOOC—C₆H₄— | ⁿPr— |
| 2-ⁱBuOOC—C₆H₄— | ⁿPr— |
| 3-ⁱBuOOC—C₆H₄— | ⁿPr— |
| 4-ⁱBuOOC—C₆H₄— | ⁿPr— |
| 2-ᵗBuOOC—C₆H₄— | ⁿPr— |
| 3-ᵗBuOOC—C₆H₄— | ⁿPr— |
| 4-ᵗBuOOC—C₆H₄— | ⁿPr— |
| 2-Me-3-Me—C₆H₃— | ⁿPr— |
| 2-Me-4-Me—C₆H₃— | ⁿPr— |
| 2-Me-5-Me—C₆H₃— | ⁿPr— |
| 2-Me-6-Me—C₆H₃— | ⁿPr— |
| 3-Me-4-Me—C₆H₃— | ⁿPr— |
| 3-Me-5-Me—C₆H₃— | ⁿPr— |
| 3-Me-6-Me—C₆H₃— | ⁿPr— |
| 2-MeO-3-MeO—C₆H₃— | ⁿPr— |
| 2-MeO-4-MeO—C₆H₃— | ⁿPr— |
| 2-MeO-5-MeO—C₆H₃— | ⁿPr— |
| 2-MeO-6-MeO—C₆H₃— | ⁿPr— |
| 3-MeO-4-MeO—C₆H₃— | ⁿPr— |
| 3-MeO-5-MeO—C₆H₃— | ⁿPr— |
| 3-MeO-6-MeO—C₆H₃— | ⁿPr— |
| Ph—CH₂CH₂— | ⁿPr— |
| Ph—CH₂CH₂CH₂— | ⁿPr— |
| Ph—CH₂CH₂CH₂CH₂— | ⁿPr— |
| CH₃(CH₂)₈— | ⁿPr— |
| CH₃(CH₂)₇— | ⁿPr— |
| CH₃(CH₂)₆— | ⁿPr— |
| CH₃(CH₂)₅— | ⁿPr— |
| CH₃(CH₂)₄— | ⁿPr— |
| CH₃(CH₂)₃— | ⁿPr— |
| CH₃(CH₂)₂— | ⁿPr— |
| CH₃(CH₂)₉— | ⁿPr— |
| (CH₃)₂CH(CH₂)₇— | ⁿPr— |
| (CH₃)₂CH(CH₂)₆— | ⁿPr— |
| (CH₃)₂CH(CH₂)₅— | ⁿPr— |
| (CH₃)₂CH(CH₂)₄— | ⁿPr— |
| (CH₃)₂CH(CH₂)₃— | ⁿPr— |
| (CH₃)₂CH(CH₂)₂— | ⁿPr— |
| (CH₃)₃C(CH₂)₆— | ⁿPr— |
| (CH₃)₃C(CH₂)₅— | ⁿPr— |
| (CH₃)₃C(CH₂)₄— | ⁿPr— |
| (CH₃)₃C(CH₂)₃— | ⁿPr— |
| (CH₃)₃C(CH₂)₂— | ⁿPr— |
| CH₃(CH₂)₇(CH₃)CH— | ⁿPr— |
| CH₃(CH₂)₆(CH₃)CH— | ⁿPr— |
| CH₃(CH₂)₅(CH₃)CH— | ⁿPr— |
| CH₃(CH₂)₄(CH₃)CH— | ⁿPr— |
| CH₃(CH₂)₃(CH₃)CH— | ⁿPr— |
| CH₃(CH₂)₂(CH₃)CH— | ⁿPr— |
| CH₃(CH₂)₆(CH₃)CHCH₂— | ⁿPr— |
| CH₃(CH₂)₅(CH₃)CHCH₂— | ⁿPr— |
| CH₃(CH₂)₄(CH₃)CHCH₂— | ⁿPr— |
| CH₃(CH₂)₃(CH₃)CHCH₂— | ⁿPr— |
| CH₃(CH₂)₂(CH₃)CHCH₂— | ⁿPr— |
| Ph— | ⁱPr— |
| Ph— | ⁿBu— |
| Ph— | ⁱBu— |
| Ph— | Et— |
| Ph— | Me— |
| 4-PhO—C₆H₄— | H |
| 3-PhO—C₆H₄— | H |
| 3-Cl₃C—C₆H₄— | H |
| 4-Cl₃C—C₆H₄— | H |
| 3-MeO-4-MeO-5-MeO—C₆H₂— | H |
| 3-Me-4-Me-5-Me—C₆H₂— | H |
| 2-Cl-3-Cl—C₆H₃— | H |
| 2-Cl-4-Cl—C₆H₃— | H |
| 2-Cl-5-Cl—C₆H₃— | H |
| 2-Cl-6-Cl—C₆H₃— | H |
| 3-Cl-5-Cl—C₆H₃— | H |
| 3-Cl-6-Cl—C₆H₃— | H |
| 3-Cl-4-Cl—C₆H₃— | H |
| 2-MeO—C₆H₄—CH₂CH₂— | H |
| 3-MeO—C₆H₄—CH₂CH₂— | H |
| 4-MeO—C₆H₄—CH₂CH₂— | H |
| 2-EtO—C₆H₄—CH₂CH₂— | H |
| 3-EtO—C₆H₄—CH₂CH₂— | H |
| 4-EtO—C₆H₄—CH₂CH₂— | H |
| 2-F—C₆H₄—CH₂CH₂— | H |
| 3-F—C₆H₄—CH₂CH₂— | H |
| 4-F—C₆H₄—CH₂CH₂— | H |
| 2-Cl—C₆H₄—CH₂CH₂— | H |
| 3-Cl—C₆H₄—CH₂CH₂— | H |
| 4-Cl—C₆H₄—CH₂CH₂— | H |
| 2-Br—C₆H₄—CH₂CH₂— | H |
| 3-Br—C₆H₄—CH₂CH₂— | H |
| 4-Br—C₆H₄—CH₂CH₂— | H |
| 2-F₃C—C₆H₄—CH₂CH₂— | H |
| 3-F₃C—C₆H₄—CH₂CH₂— | H |
| 4-F₃C—C₆H₄—CH₂CH₂— | H |
| 2-F₃CO—C₆H₄—CH₂CH₂— | H |
| 3-F₃CO—C₆H₄—CH₂CH₂— | H |
| 4-F₃CO—C₆H₄—CH₂CH₂— | H |
| 2-Me—C₆H₄—CH₂CH₂— | H |
| 3-Me—C₆H₄—CH₂CH₂— | H |
| 4-Me—C₆H₄—CH₂CH₂— | H |
| 2-Et—C₆H₄—CH₂CH₂— | H |
| 3-Et—C₆H₄—CH₂CH₂— | H |
| 4-Et—C₆H₄—CH₂CH₂— | H |
| 2-MeOOC—C₆H₄—CH₂CH₂— | H |
| 3-MeOOC—C₆H₄—CH₂CH₂— | H |
| 4-MeOOC—C₆H₄—CH₂CH₂— | H |
| 2-EtOOC—C₆H₄—CH₂CH₂— | H |
| 3-EtOOC—C₆H₄—CH₂CH₂— | H |
| 4-EtOOC—C₆H₄—CH₂CH₂— | H |
| 2-Me-3-Me—C₆H₃—CH₂CH₂— | H |
| 2-Me-4-Me—C₆H₃—CH₂CH₂— | H |
| 2-Me-5-Me—C₆H₃—CH₂CH₂— | H |
| 2-Me-6-Me—C₆H₃—CH₂CH₂— | H |
| 3-Me-4-Me—C₆H₃—CH₂CH₂— | H |
| 3-Me-5-Me—C₆H₃—CH₂CH₂— | H |
| 3-Me-6-Me—C₆H₃—CH₂CH₂— | H |
| 2-MeO-3-MeO—C₆H₃—CH₂CH₂— | H |
| 2-MeO-4-MeO—C₆H₃—CH₂CH₂— | H |
| 2-MeO-5-MeO—C₆H₃—CH₂CH₂— | H |
| 2-MeO-6-MeO—C₆H₃—CH₂CH₂— | H |
| 3-MeO-4-MeO—C₆H₃—CH₂CH₂— | H |
| 3-MeO-5-MeO—C₆H₃—CH₂CH₂— | H |
| 3-MeO-6-MeO—C₆H₃—CH₂CH₂— | H |
| 2-Cl-3-Cl—C₆H₃—CH₂CH₂— | H |
| 2-Cl-4-Cl—C₆H₃—CH₂CH₂— | H |
| 2-Cl-5-Cl—C₆H₃—CH₂CH₂— | H |
| 2-Cl-6-Cl—C₆H₃—CH₂CH₂— | H |
| 3-Cl-5-Cl—C₆H₃—CH₂CH₂— | H |
| 3-Cl-6-Cl—C₆H₃—CH₂CH₂— | H |
| 3-Cl-4-Cl—C₆H₃—CH₂CH₂— | H |
| adamantyl | H |

Table 2 lists the structures, physical properties and ¹H NMR data of the specific compounds 1 to 23 synthesized in the present invention, and the present invention is not limited to these compounds.

TABLE 2

| No | Structure | Physical properties | $^1$H NMR (400 MHz, CDCl$_3$), δ |
|---|---|---|---|
| 1 | 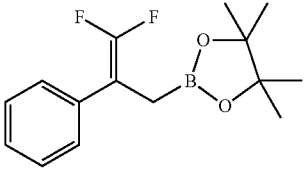 [SMILES: CC1(C)OB(CC(=C(F)F)c2ccccc2)OC1(C)C] | Colorless liquid | 7.38-7.30 (m, 4H, ArH), 7.24-7.21 (m, 1H, ArH), 1.95 (t, J = 2.5 Hz, 2H, BCH$_2$), 1.15 (s, 12H, 2C(CH$_3$)$_2$). |
| 2 | 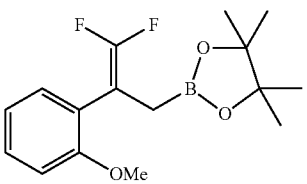 [SMILES: COc1ccccc1C(CB1OC(C)(C)C(C)(C)O1)=C(F)F] | Colorless liquid | 7.26-7.22 (m, 2H, ArH), 6.92-6.86 (m, 2H, ArH), 3.82 (s, 3H, OCH$_3$), 1.91 (t, J = 2.4 Hz, 2H, BCH$_2$), 1.14 (s, 12H, 2C(CH$_3$)$_2$). |
| 3 | 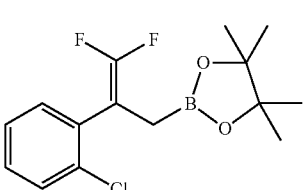 | Colorless liquid | 7.40-7.32 (m, 2H, ArH), 7.24-7.20 (m, 2H, ArH), 1.92 (t, J = 2.2 Hz, 2H, BCH$_2$), 1.16 (s, 12H, 2C(CH$_3$)$_2$). |
| 4 | 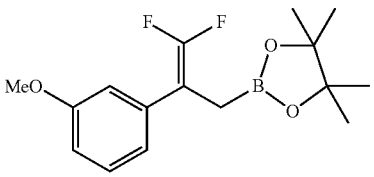 [SMILES: COc1cccc(C(CB2OC(C)(C)C(C)(C)O2)=C(F)F)c1] | Colorless liquid | 7.28-7.24 (m, 1H, ArH), 6.98-6.95 (m, 2H, ArH), 6.82-6.80 (m, 1H, ArH), 3.82 (s, 3H, OCH$_3$) 1.96 (t, J = 2.3 Hz, 2H, BCH$_2$), 1.19 (s, 12H, 2C(CH$_3$)$_2$). |
| 5 | 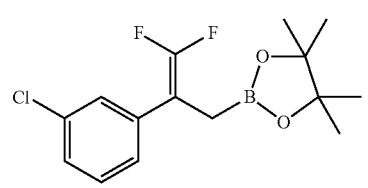 [SMILES: CC1(C)OB(CC(=C(F)F)c2cccc(Cl)c2)OC1(C)C] | Colorless liquid | 7.36 (s, 1H, ArH), 7.28-7.20 (m, 3H, ArH), 1.92 (br, 2H, BCH$_2$), 1.16 (s, 12H, 2C(CH$_3$)$_2$). |
| 6 | 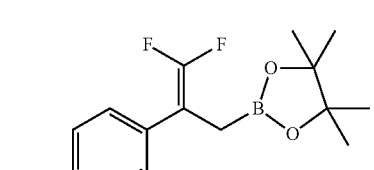 | Colorless liquid | 7.28 (d, J = 8.6 Hz, 2H, ArH), 6.86 (d, J = 8.6 Hz, 2H, ArH), 3.80 (s, 3H, OCH$_3$) 1.91 (br, 2H, BCH$_2$), 1.16 (s, 12H, 2C(CH$_3$)$_2$). |
| 7 | 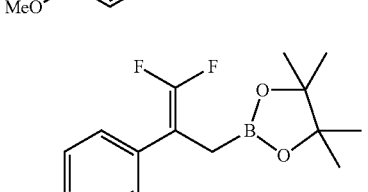 | Colorless liquid | 7.29 (s, 4H, ArH), 1.92 (t, J = 2.5 Hz, 2H, BCH$_2$), 1.15 (s, 12H, 2C(CH$_3$)$_2$). |
| 8 | 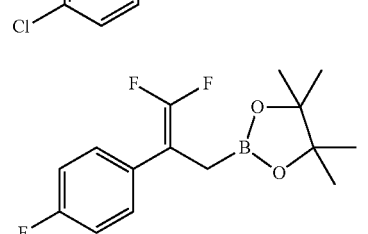 | Colorless liquid | 7.34-7.30 (m, 2H, ArH), 7.01 (t, J = 8.6 Hz, 2H, ArH), 1.92 (br, 2H, BCH$_2$), 1.15 (s, 12H, 2C(CH$_3$)$_2$). |

TABLE 2-continued

| No | Structure | Physical properties | $^1$H NMR (400 MHz, CDCl$_3$), δ |
|----|-----------|---------------------|----------------------------------|
| 9  | 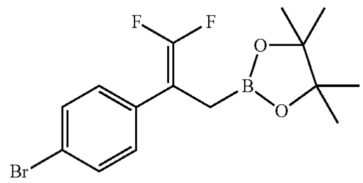 [SMILES: CC1(C)OB(CC(=C(F)F)c2ccc(Br)cc2)OC1(C)C]          | Colorless liquid | 7.46-7.43 (m, 2H, ArH), 7.24-7.21 (m, 2H, ArH), 1.92 (t, J = 2.4 Hz, 2H, BCH$_2$), 1.16 (s, 12H, 2C(CH$_3$)$_2$). |
| 10 | 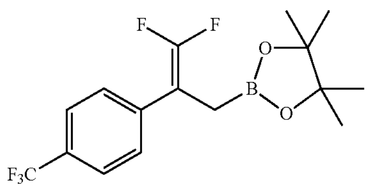 [SMILES: CC1(C)OB(CC(=C(F)F)c2ccc(C(F)(F)F)cc2)OC1(C)C]          | Colorless liquid | 7.58 (d, J = 8.2 Hz, 2H, ArH), 7.48 (d, J = 8.2 Hz, 2H, ArH), 1.96 (br, 2H, BCH$_2$), 1.16 (s, 12H, 2C(CH$_3$)$_2$). |
| 11 | 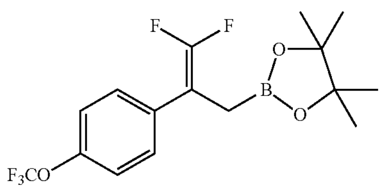 [SMILES: CC1(C)OB(CC(=C(F)F)c2ccc(OC(F)(F)F)cc2)OC1(C)C]          | Colorless liquid | 7.38 (d, J = 8.6 Hz, 2H, ArH), 7.17 (d, J = 8.4 Hz, 2H, ArH), 1.94 (br, 2H, BCH$_2$), 1.14 (s, 12H, 2C(CH$_3$)$_2$). |
| 12 | 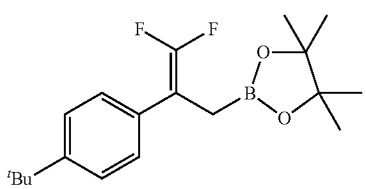 [SMILES: CC(C)(C)c1ccc(C(CB2OC(C)(C)C(C)(C)O2)=C(F)F)cc1]          | Colorless liquid | 7.28-7.26 (m, 2H, ArH), 7.23-7.18 (m, 2H, ArH), 1.86 (t, J = 2.4 Hz, 2H, BCH$_2$), 1.23 (s, 9H, C(CH$_3$)$_3$), 1.07 (s, 12H, 2C(CH$_3$)$_2$). |
| 13 | 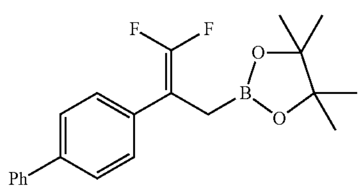          | White solid Melting point: 61-62° C. | 7.61-7.56 (m, 4H, ArH), 7.46-7.42 (m, 4H, ArH), 7.37-7.33 (m, 1H, ArH), 1.99 (t, J = 2.5 Hz, 2H, ArCH$_2$), 1.17 (s, 12H, 2C(CH$_3$)$_2$). |
| 14 | 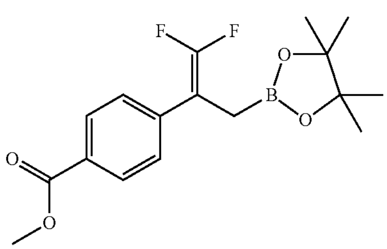 [SMILES: COC(=O)c1ccc(C(CB2OC(C)(C)C(C)(C)O2)=C(F)F)cc1]          | Colorless liquid | 7.99 (d, J = 8.0 Hz, 2H, ArH), 7.43 (d, J = 8.2 Hz, 2H, ArH), 3.91 (s, 3H, OCH$_3$), 1.96 (br, 2H, BCH$_2$), 1.14 (s, 12H, 2C(CH$_3$)$_2$). |
| 15 | 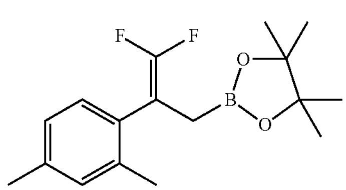          | Colorless liquid | 7.11 (d, J = 7.8 Hz, 1H, ArH), 7.01 (s, 1H, ArH), 6.97 (d, J = 7.8 Hz, 1H, ArH), 2.29 (s, 3H, ArCH$_3$), 2.27 (s, 3H, ArCH$_3$), 1.84 (br, 2H, BCH$_2$), 1.17 (s, 12H, 2C(CH$_3$)$_2$). |

TABLE 2-continued

| No | Structure | Physical properties | $^1$H NMR (400 MHz, CDCl$_3$), δ |
|---|---|---|---|
| 16 | 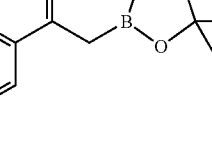 | Colorless liquid | 6.98 (s, 2H, ArH), 6.87 (s, 1H, ArH), 2.30 (s, 6H, 2ArCH$_3$), 1.92 (t, J = 2.4 Hz, 2H, BCH$_2$), 1.17 (s, 12H, 2C(CH$_3$)$_2$). |
| 17 | 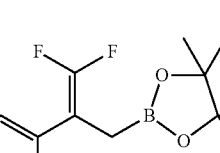 | Colorless liquid | 6.88 (t, J = 1.3 Hz, 1H, ArH), 6.82-6.75 (m, 2H, ArH), 5.94 (s, 2H, OCH$_2$), 1.89 (t, J = 2.6 Hz, 2H, BCH$_2$), 1.17 (s, 12H, 2C(CH$_3$)$_2$). |
| 18 | 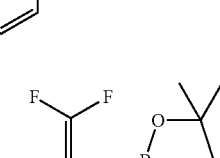 | Pale yellow solid Melting point: 78-79° C. | 7.77 (d, J = 7.6 Hz, 1H, ArH), 7.71-7.69 (m, 1H, ArH), 7.34-7.24 (m, 3H, ArH), 2.05 (br, 2H, BCH$_2$), 1.20 (s, 12H, 2C(CH$_3$)$_2$). |
| 19 | 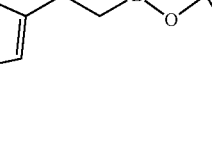 | Colorless liquid | 8.00 (d, J = 8.6 Hz, 1H, ArH), 7.87-7.85 (m, 1H, ArH), 7.82-7.80 (m, 1H, ArH), 7.54-7.44 (m, 4H, ArH), 2.04 (br, 2H, BCH$_2$), 1.12 (s, 12H, 2C(CH$_3$)$_2$). |
| 20 | 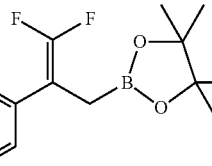 | Colorless liquid | 7.30-7.26 (m, 2H, ArH), 7.20-7.18 (m, 3H, ArH), 2.70 (t, J = 8.1 Hz, 2H, CH$_2$), 2.30 (t, J = 8.1 Hz, 2H, CH$_2$), 1.57 (br, 2H, BCH$_2$), 1.26 (s, 12H, 2C(CH$_3$)$_2$). |
| 21 | 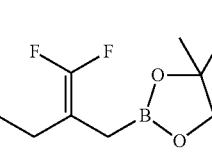 | Colorless liquid | 7.25-7.21 (m, 4H, ArH), 7.20-7.14 (m, 1H, ArH), 2.06 (t, J = 7.7 Hz, 1H, BCH), 1.62-1.52 (m, 1H, CH), 1.41-1.19 (m, 3H, CH + CH$_2$), 1.14 (s, 6H, C(CH$_3$)$_2$), 1.12 (s, 6H, C(CH$_3$)$_2$), 0.79 (t, 3H, J = 7.3 Hz, CH$_2$CH$_3$). |
| 22 | 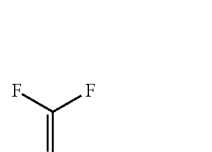 | Colorless liquid | 1.98 (t, J = 7.4 Hz, 2H, CCH$_2$), 1.51 (br, 2H, BCH$_2$), 1.40-1.24 (m, 26H, 7CH$_2$ + 2C(CH$_3$)$_2$), 0.88 (t, J= 6.6 Hz, 3H, CH$_2$CH$_3$). |

TABLE 2-continued

| No | Structure | Physical properties | $^1$H NMR (400 MHz, CDCl$_3$), δ |
|---|---|---|---|
| 23 | 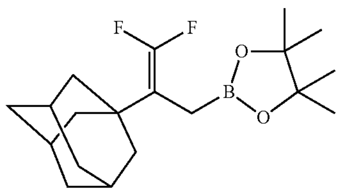 [SMILES: CC1(C)OB(CC(=C(F)F)C23CC4CC(CC(C4)C2)C3)OC1(C)C] | Colorless liquid | 1.97 (br, 3H, 3CH), 1.78 (br, 6H, 3CH$_2$), 1.67 (br, 6H, 3CH$_2$), 1.47 (br, 2H, BCH$_2$), 1.24 (s, 12H, 2C(CH$_3$)$_2$). |

Beneficial effects of the present invention: iron is the second highest metal element in the earth's crust and an indispensable trace element in the human body, and has the advantages of rich content, low-cost, easy availability, low toxicity and environmental friendliness, and the catalysts developed based on iron can meet the current requirements for sustainable development and green chemistry. In the method of the present invention, a cheap commercially available metal iron salt is used as a catalyst to provide a convenient, low-cost method for preparing difluoroallylboronate, and provide a new and effective approach for the synthesis of γ-aminobutyric acid receptor agonist (III).

DETAILED DESCRIPTIONS OF THE PREFERRED EMBODIMENTS

The following non-limiting embodiments are provided to enable a person of ordinary skill in the art to understand the invention, but not to limit the invention in any way.

The test methods described in the following embodiments are conventional methods unless otherwise specified; the reagents and materials are commercially available unless otherwise specified.

Embodiment 1

Preparation of 2-phenyl-3,3-difluoroallyl-4,4,5,5-tetramethyl-1,3,2-dioxaborolane (Compound 1)

At room temperature, successively add 6.3 mg of catalyst FeCl$_2$ (0.05 mmol, 5% of the amount of substance of α-trifluoromethylstyrene, record as 5 mol %), 8 mL of anhydrous THF, 172 mg of α-trifluoromethylstyrene (1 mmol), 279 mg of bis(pinacolato)diboron (1.1 mmol, 1.1 times of molar amount of α-trifluoromethylstyrene,), 88 mg of lithium tert-butoxide (1.1 mmol, 1.1 times of molar amount of α-trifluoromethylstyrene) in turn to a 25 mL Schlenk bottle with the protection of argon gas. The reaction system is pale yellow turbid solution. Place the solution at 65° C. to react for 12 hours. After the solvent is removed by a rotary evaporator, add 25 mL of water, and extract it with ethyl acetate (3×15 mL), combine the organic phases and wash them with NaCl saturated solution (2×10 mL), then dry it over anhydrous Na$_2$SO4, and obtain the target compound through column chromatography, the packing material is silica gel, the eluent is petroleum ether:ethyl acetate (50:1), and an isolated yield is 92%.

Embodiment 2

Preparation of 2-(2-methoxyphenyl)-3,3-difluoroallyl-4,4,5,5-tetramethyl-1,3,2-dioxaborolane (Compound 2)

The procedures are the same as those in the Embodiment 1 except that the α-trifluoromethylstyrene is changed to the same molar amount of 2-methoxyl-α-trifluoromethylstyrene, to obtain the target compound with an isolated yield of 89%.

Embodiment 3

Preparation of 2-(2-chlorophenyl)-3,3-difluoroallyl-4,4,5,5-tetramethyl-1,3,2-dioxaborolane (Compound 3)

The procedures are the same as those in the Embodiment 1 except that the α-trifluoromethylstyrene is changed to the same molar amount of 2-chloro-α-trifluoromethylstyrene, to obtain the target compound with an isolated yield of 72%.

Embodiment 4

Preparation of 2-(3-methoxyphenyl)-3,3-difluoroallyl-4,4,5,5-tetramethyl-1,3,2-dioxaborolane (Compound 4)

The procedures are the same as those in the Embodiment 1 except that the α-trifluoromethylstyrene is changed to the same molar amount of 3-methoxyl-α-trifluoromethylstyrene, to obtain the target compound with an isolated yield of 90%.

Embodiment 5

Preparation of 2-(3-chlorophenyl)-3,3-difluoroallyl-4,4,5,5-tetramethyl-1,3,2-dioxaborolane (Compound 5)

The procedures are the same as those in the Embodiment 1 except that the α-trifluoromethylstyrene is changed to the same molar amount of 3-chloro-α-trifluoromethylstyrene, to obtain the target compound with an isolated yield of 69%.

Embodiment 6

Preparation of 2-(4-methoxyphenyl)-3,3-difluoroallyl-4,4,5,5-tetramethyl-1,3,2-dioxaborolane (Compound 6)

The procedures are the same as those in the Embodiment 1 except that the α-trifluoromethylstyrene is changed to the same molar amount of 4-methoxyl-α-trifluoromethylstyrene, to obtain the target compound with an isolated yield of 80%.

Embodiment 7

Preparation of 2-(4-chlorophenyl)-3,3-difluoroallyl-4,4,5,5-tetramethyl-1,3,2-dioxaborolane (Compound 7)

The procedures are the same as those in the Embodiment 1 except that the α-trifluoromethylstyrene is changed to the same molar amount of 4-chloro-α-trifluoromethylstyrene, to obtain the target compound with an isolated yield of 96%.

Embodiment 8

Preparation of 2-(4-fluorophenyl)-3,3-difluoroallyl-4,4,5,5-tetramethyl-1,3,2-dioxaborolane (Compound 8)

The procedures are the same as those in the Embodiment 1 except that the α-trifluoromethylstyrene is changed to the same molar amount of 4-fluoro-α-trifluoromethylstyrene, to obtain the target compound with an isolated yield of 84%.

Embodiment 9

Preparation of 2-(4-bromophenyl)-3,3-difluoroallyl-4,4,5,5-tetramethyl-1,3,2-dioxaborolane (Compound 9)

The procedures are the same as those in the Embodiment 1 except that the α-trifluoromethylstyrene is changed to the same molar amount of 4-bromo-α-trifluoromethylstyrene, to obtain the target compound with an isolated yield of 84%.

Embodiment 10

Preparation of 2-(4-trifluoromethylphenyl)-3,3-difluoroallyl-4,4,5,5-tetramethyl-1,3,2-dioxaborolane (Compound 10)

The procedures are the same as those in the Embodiment 1 except that the α-trifluoromethylstyrene is changed to the same molar amount of 4-trifluoromethyl-α-trifluoromethylstyrene, to obtain the target compound with an isolated yield of 86%.

Embodiment 11

Preparation of 2-(4-trifluoromethoxyphenyl)-3,3-difluoroallyl-4,4,5,5-tetramethyl-1,3,2-dioxaborolane (Compound 11)

The procedures are the same as those in the Embodiment 1 except that the α-trifluoromethylstyrene is changed to the same molar amount of 4-trifluoromethoxy-α-trifluoromethylstyrene, to obtain the target compound with an isolated yield of 97%.

Embodiment 12

Preparation of 2-(4-tert-butylphenyl)-3,3-difluoroallyl-4,4,5,5-tetramethyl-1,3,2-dioxaborolane (Compound 12)

The procedures are the same as those in the Embodiment 1 except that the α-trifluoromethylstyrene is changed to the same molar amount of 4-tert-butyl-α-trifluoromethylstyrene, to obtain the target compound with an isolated yield of 86%.

Embodiment 13

Preparation of 2-(4-phenylphenyl)-3,3-difluoroallyl-4,4,5,5-tetramethyl-1,3,2-dioxaborolane (Compound 13)

The procedures are the same as those in the Embodiment 1 except that the α-trifluoromethylstyrene is changed to the same molar amount of 4-phenyl-α-trifluoromethylstyrene, to obtain the target compound with an isolated yield of 95%.

Embodiment 14

Preparation of 2-(4-methoxycarbonylphenyl)-3,3-difluoroallyl-4,4,5,5-tetramethyl-1,3,2-dioxaborolane (Compound 14)

The procedures are the same as those in the Embodiment 1 except that the α-trifluoromethylstyrene is changed to the same molar amount of 4-methoxycarbonyl-α-trifluoromethylstyrene, to obtain the target compound, with an isolated yield of 58%.

Embodiment 15

Preparation of 2-(2,4-dimethylphenyl)-3,3-difluoroallyl-4,4,5,5-tetramethyl-1,3,2-dioxaborolane (Compound 15)

The procedures are the same as those in the Embodiment 1 except that the α-trifluoromethylstyrene is changed to the same molar amount of 3,4-methylenedioxy-α-trifluoromethylstyrene, to obtain the target compound with an isolated yield of 99%.

Embodiment 16

Preparation of 2-(3,5-dimethylphenyl)-3,3-difluoroallyl-4,4,5,5-tetramethyl-1,3,2-dioxaborolane (Compound 16)

The procedures are the same as those in the Embodiment 1 except that the α-trifluoromethylstyrene is changed to the same molar amount of 2,4-dimethyl-α-trifluoromethylstyrene, to obtain the target compound, with an isolated yield of 73%.

Embodiment 17

Preparation of 2-(3,4-methylenedioxyphenyl)-3,3-difluoroallyl-4,4,5,5-tetramethyl-1,3,2-dioxaborolane (Compound 17)

The procedures are the same as those in the Embodiment 1 except that the α-trifluoromethylstyrene is changed to the same molar amount of 3,5-dimethyl-α-trifluoromethylstyrene, to obtain the target compound with an isolated yield of 80%.

Embodiment 18

Preparation of 2-(benzothiophen-2-yl)-3,3-difluoro-allyl-4,4,5,5-tetramethyl-1,3,2-dioxaborolane (Compound 18)

The procedures are the same as those in the Embodiment 1 except that the α-trifluoromethylstyrene is changed to the same molar amount of α-trifluoromethyl-2-benzothiophene ethylene, to obtain the target compound with an isolated yield of 73%.

Embodiment 19

Preparation of 2-(1-naphthyl)-3,3-difluoroallyl-4,4,5,5-tetramethyl-1,3,2-dioxaborolane (Compound 19)

The procedures are the same as those in the Embodiment 1 except that the α-trifluoromethylstyrene is changed to the same molar amount of α-trifluoromethyl-1-vinylnaphthalene, to obtain the target compound with an isolated yield of 72%.

Embodiment 20

Preparation of 2-(2-phenylethyl)-3,3-difluoroallyl-4,4,5,5-tetramethyl-1,3,2-dioxaborolane (Compound 20)

The procedures are the same as those in the Embodiment 1 except that the α-trifluoromethylstyrene is changed to the same molar amount of 2-trifluoromethyl-4-phenyl-1-butene, to obtain the target compound with an isolated yield of 94%.

Embodiment 21

Preparation of 2-(1,1-difluoro-2-phenylhex-1-en-3-yl)-4,4,5,5-tetramethyl-1,3,2-dioxaborolane (Compound 21)

The procedures are the same as those in the Embodiment 1 except that the α-trifluoromethylstyrene is changed to the same molar amount of 1-trifluoromethyl-1-phenylpentene (the mixture of the cis-trans isomerism, with a ratio of cis isomer to trans isomer at 1:2.16), to obtain the target compound with an isolated yield of 67%.

Embodiment 22

Preparation of 2-(2-(difluoromethylene)undecyl)-4,4,5,5-tetramethyl-1,3,2-dioxaborolane (Compound 22)

The procedures are the same as those in the Embodiment 1 except that the α-trifluoromethylstyrene is changed to the same molar amount of 2-trifluoromethyl-1-hendecene, to obtain the target compound with an isolated yield of 91%.

Embodiment 23

Preparation of 2-(2-((3r,5r,7r)-adamantan-1-yl)-3,3-difluoroallyl)-4,4,5,5-tetramethyl-1,3,2-dioxaborolane (Compound 23)

The procedures are the same as those in the Embodiment 1 except that the α-trifluoromethylstyrene is changed to the same molar amount of 3,3,3-trifluoro-2-(adamantane-1-yl) propene, to obtain the target compound with an isolated yield of 76%.

Embodiment 24

Preparation of 2-phenyl-3,3-difluoroallyl-4,4,5,5-tetramethyl-1,3,2-dioxaborolane (Compound 1)

The procedures are the same as those in the Embodiment 1 except that the anhydrous THF is changed to anhydrous acetonitrile, to obtain the target compound with a H-NMR yield of 18% (1,1,2,2-tetrachloroethane is used as an internal standard).

Embodiment 25

Preparation of 2-phenyl-3,3-difluoroallyl-4,4,5,5-tetramethyl-1,3,2-dioxaborolane (Compound 1)

The procedures are the same as those in the Embodiment 1 except that the anhydrous THF is changed to anhydrous glycol dimethyl ether, to obtain the target compound with a H-NMR yield of 93% (1,1,2,2-tetrachloroethane is used as an internal standard).

Embodiment 26

Preparation of 2-phenyl-3,3-difluoroallyl-4,4,5,5-tetramethyl-1,3,2-dioxaborolane (Compound 1)

The procedures are the same as those in the Embodiment 1 except that lithium tert-butoxide is changed to potassium methoxide, to obtain the target compound with a H-NMR yield of 45% (1,1,2,2-tetrachloroethane is used as an internal standard).

Embodiment 27

Preparation of 2-phenyl-3,3-difluoroallyl-4,4,5,5-tetramethyl-1,3,2-dioxaborolane (Compound 1)

The procedures are the same as those in the Embodiment 1 except that the molar amount of the lithium tert-butoxide is reduced to 0.6 time, to obtain the target compound with a H-NMR yield of 60% (1,1,2,2-tetrachloroethane is used as an internal standard).

Embodiment 28

Preparation of 2-phenyl-3,3-difluoroallyl-4,4,5,5-tetramethyl-1,3,2-dioxaborolane (Compound 1)

The procedures are the same as those in the Embodiment 1 except that the molar amount of bis(pinacolato)diboron is reduced to 0.6 time, to obtain the target compound with a H-NMR yield of 59% (1,1,2,2-tetrachloroethane is used as an internal standard).

Embodiment 29

Preparation of 2-phenyl-3,3-difluoroallyl-4,4,5,5-tetramethyl-1,3,2-dioxaborolane (Compound 1)

The procedures are the same as those in the Embodiment 1 except that the catalyst $FeCl_2$ is reduced to 1 mol %, to obtain the target compound with a H-NMR yield of 17% (1,1,2,2-tetrachloroethane is used as an internal standard).

Embodiment 30

Preparation of 2-phenyl-3,3-difluoroallyl-4,4,5,5-tetramethyl-1,3,2-dioxaborolane (Compound 1)

The procedures are the same as those in the Embodiment 1 except that the catalyst $FeCl_2$ is changed to 10 mol %, to obtain the target compound with a H-NMR yield of 99% (1,1,2,2-tetrachloroethane is used as an internal standard).

Embodiment 31

Preparation of 2-phenyl-3,3-difluoroallyl-4,4,5,5-tetramethyl-1,3,2-dioxaborolane (Compound 1)

The procedures are the same as those in the Embodiment 1 except that the reaction temperature is reduced to 25° C., to the target compound with a H-NMR yield of 34% (1,1,2,2-tetrachloroethane is used as an internal standard).

Embodiment 32

Synthesis of 3-(4-acetylphenyl)-1-((3r,5r,7r)-adamantan-1-yl)-2,2-difluoro-3-hydroxypropan-1-one (Compound III)

① Successively add 85 mg of 2-(2-((3r,5r,7r)-adamantan-1-yl)-3,3-difluoroallyl)-4,4,5,5-tetramethyl-1,3,2-dioxaborolane (0.2513 mmol), 3 mL of toluene, 37 mg of 4-acetylbenzaldehyde (0.2513 mmol), 6 mg of 10 mol % diphenyl phosphate (0.02513 mmol), and 3 mg of 10 mol % benzoic acid (0.02513 mmol) to a 25 mL Schlenk bottle in an argon atmosphere, sealing the bottle and transfer it to an oil bath at 60° C. react for 24 h. After cooling, the mixture is directly subjected to silica gel column chromatography, with the eluent of petroleum ether:ethyl acetate (5:1), to obtain 58 mg of 1-(4-(3-((3r,5r,7r)-adamantan-1-yl)-2,2-difluoro-1-hydroxybut-3-en-1-yl)phenyl)ethanone with a yield of 64%.

White solid, m.p. 116-118° C., $^1$H NMR: δ7.94 (d, J=7.9 Hz, 2H, ArH), 7.53 (d, J=7.9 Hz, 2H, ArH), 5.36 (s, 1H, ½CCH$_2$), 5.25 (s, 1H, ½CCH$_2$), 5.04 (dd, J=10.0 Hz, J=13.6 Hz, 1H, ArCH), 3.61 (br, 4H, OH+CH$_3$), 2.02 (br, 3H, 3CH), 1.80 (br, 6H, 3CH$_2$), 1.70 (m, 6H, 3CH$_2$).

② Successively add 20 mg of 1-(4-(3-((3r,5r,7r)-adamantan-1-yl)-2,2-difluoro-1-hydroxybut-3-en-1-yl)phenyl)ethanone (0.05553 mmol), 3 mL of dichloromethane, 1.5 mL of methanol to a 25 mL Schlenk bottle, cool to −78° C. and introduce ozone by bubbling, and maintain the colour of blue for 10 min, then transfer the bottle at room temperature and introduce argon gas by bubbling until the reaction system becomes colorless and clear solution. Cool down again to −78° C. and keep argon atmosphere, add 7 mg of dimethyl sulfide (0.1110 mmol), naturally rise to the room temperature to react 18 h. Then the mixture is directly subjected to silica gel column chromatography, with the eluent of petroleum ether:ethyl acetate (5:1), to obtain 19 mg of compound III with a yield of 95%.

White solid, m.p. 97-99° C., $^1$H NMR: δ7.94 (d, J=7.4 Hz, 2H, ArH), 7.52 (d, J=7.9 Hz, 2H, ArH), 5.32 (dd, J=6.1 Hz, J=18.0 Hz, 1H, ArCH), 3.28 (br, 1H, OH), 2.59 (s, 3H, CH$_3$), 2.02 (br, 3H, 3CH), 1.89 (br, 6H, 3CH$_2$), 1.70 (m, 6H, 3CH$_2$).

Embodiment 33

Synthesis of 3-(4-acetylphenyl)-1-((3r,5r,7r)-adamantan-1-yl)-2,2-difluoro-3-hydroxypropan-1-one (Compound III)

① Successively add 169 mg of 2-(2-((3r,5r,7r)-adamantan-1-yl)-3,3-difluoroallyl)-4,4,5,5-tetramethyl-1,3,2-dioxaborolane (0.5 mmol), 3 mL of toluene, 111 mg of 4-acetylbenzaldehyde (0.75 mmol), 12 mg of 10 mol % diphenyl phosphate (0.05 mmol), and 6 mg of 10 mol % benzoic acid (0.05 mmol) to a 25 mL Schlenk bottle in an argon atmosphere, sealing the bottle and transfer to an oil bath at 65° C. react for 13 h. After cooling, the mixture is directly subjected to silica gel column chromatography, with the eluent of petroleum ether:ethyl acetate (5:1), to obtain 166 mg of 1-(4-(3-((3r,5r,7r)-adamantan-1-yl)-2,2-difluoro-1-hydroxybut-3-en-1-yl)phenyl)ethanone with a yield of 92%.

② Successively add 20 mg of 1-(4-(3-((3r,5r,7r)-adamantan-1-yl)-2,2-difluoro-1-hydroxybut-3-en-1-yl)phenyl)ethanone (0.05553 mmol), 3 mL of dichloromethane, 1.5 mL of methanol to a 25 mL Schlenk bottle, cool to −78° C. and introduce ozone by bubbling, and maintain the colour of blue for 10 min, then transfer the bottle at room temperature and introduce argon gas by bubbling until the reaction system becomes colorless and clear solution. Cool down again to −78° C. and keep argon atmosphere, add 7 mg of dimethyl sulfide (0.1110 mmol), naturally rise to the room temperature to react 18 h. Then the mixture is directly subjected to silica gel column chromatography, with the eluent of petroleum ether:ethyl acetate (5:1), to obtain 19 mg of compound III with a yield of 95%.

The invention claimed is:

1. A method for preparing difluoroallylboronate, using a compound of the formula II and bis (pinacolato) diboron as raw materials in a solvent in the presence of an iron catalyst and a base according to the following reaction formula, to obtain a compound of the formula I,

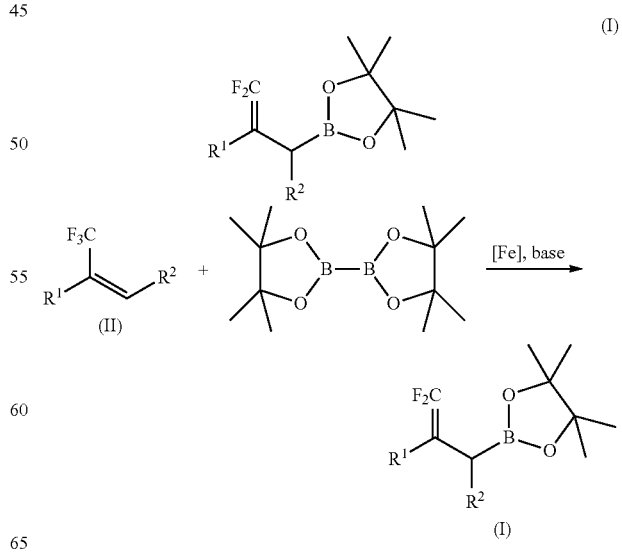

Wherein,

R$^1$ is selected from (C1-C10) alkyl,

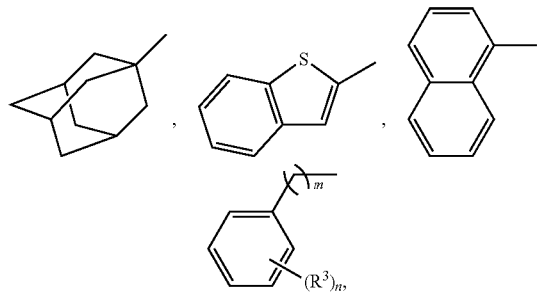

wherein, m=0-4, n=1-5;

R$^2$ is selected from H, (C1-C6) alkyl;

R$^3$ is selected from H, (C1-C6) alkyl, phenyl, halogen, trifluoromethyl, trifluoromethoxy, (C1-C4) alkoxyl, (C2-C5) ester group;

the iron catalyst is at least one of ferrous chloride, ferric chloride, ferrous bromide, ferric bromide, ferric acetylacetonate, ferrous acetylacetonate, and ferrous acetate;

the base is selected from at least one of potassium t-butoxide, sodium t-butoxide, lithium t-butoxide, sodium methoxide, lithium methoxide, potassium methoxide, cesium carbonate, potassium carbonate, sodium carbonate, sodium hydroxide, potassium hydroxide, potassium phosphate.

2. The method according to claim 1, wherein the R$^2$ is H or propyl.

3. The method according to claim 1, wherein the R$^3$ is H, methyl, methoxyl, halogen, trifluoromethyl, tert-butyl, trifluoromethoxy, phenyl.

4. The method according to claim 1, wherein the amount of substance of the base is 0.5 to 3 times of that of the compound of formula II.

5. The method according to claim 4, wherein the amount of substance of the base is 1 to 2 times of that of the compound of formula II.

6. The method according to claim 1, wherein the amount of substance of the bis (pinacolato) diboron is 1 to 3 times of that of the compound of formula II.

7. The method according to claim 6, wherein the amount of substance of the bis (pinacolato) diboron is 1 to 1.5 times of that of the compound of formula II.

8. The method according to claim 1, wherein the amount of substance of the catalyst is 0.1% to 10% of that of the compound of formula II.

9. The method according to claim 1, wherein the reaction temperature of the reaction is 25° C. to solvent reflux temperature, and the reaction time is 10 min to 48 h.

10. Application of the method for preparing the compound of the formula I claimed in claim 1 in the synthesis of γ-aminobutyric acid receptor agonist (III), wherein, synthesizing 2-(2-((3r,5r,7r)-adamantan-1-yl)-3,3-difluoroallyl)-4,4,5,5-tetramethyl-1,3,2-dioxaborolane according to the method in claim 1, and then performing the following route:

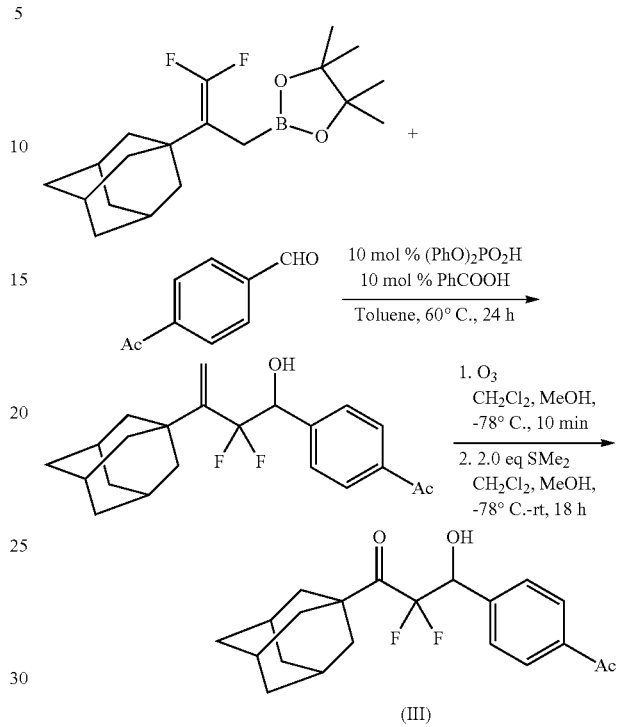

including the following two-step reaction:

① in toluene solvent, 2-(2-((3r,5r,7r)-adamantan-1-yl)-3,3-difluoroallyl)-4,4,5,5-tetramethyl-1,3,2-dioxaborolane and 4-acetylbenzaldehyde react at 60° C. for 10 h-30 h under the catalysis of diphenyl phosphate and benzoic acid, with a molar ratio of 2-(2-((3r,5r,7r)-adamantan-1-yl)-3,3-difluoroallyl)-4,4,5,5-tetramethyl-1,3,2-dioxaborolane, 4-acetylbenzaldehyde, diphenyl phosphate and benzoic acid at 1:(1-1.5):0.1:0.1;

② dissolve 1-(4-(3-((3r,5r,7r)-adamantan-1-yl)-2,2-difluoro-1-hydroxybut-3-en-1-yl)phenyl)ethanone in dichloromethane/methanol mixed solvent, introduce ozone by bubbling at −78° C. and maintain the colour of blue for 10 min, then move them to room temperature and introduce argon by bubbling until the reaction system become a colorless clear solution; then cool them to −78° C. again and add dimethyl sulfide under the argon atmosphere, naturally rise to room temperature and react for 10 h-24 h; the molar ratio of 1-(4-(3-((3r, 5r, 7r)-adamantan-1-yl)-2,2-difluoro-1-hydroxybut-3-en-1-yl)phenyl) ethanone and dimethyl sulfide is 1:2, and the volume ratio of dichloromethane and methanol in the mixed solvent is 1:1-3:1.

* * * * *